US008685704B2

(12) United States Patent
Lang et al.

(10) Patent No.: US 8,685,704 B2
(45) Date of Patent: Apr. 1, 2014

(54) MICROORGANISM FOR THE PRODUCTION OF SUCCINIC ACID (75) Inventors: Christine Lang, Berlin (DE); Markus Veen, Berlin (DE); Mewes Bottner, Berlin (DE); Andreas Raab, Berlin (DE)

(73) Assignee: Organo-Balance GmbH, Berlin (DE)

( * ) Notice: Subject to any disclaimer, the term of this patent is extended or adjusted under 35 U.S.C. 154(b) by 699 days.

(21) Appl. No.: 12/596,771

(22) PCT Filed: Apr. 16, 2008

(86) PCT No.: PCT/DE2008/000670
§ 371 (c)(1),
(2), (4) Date: Apr. 29, 2010

(87) PCT Pub. No.: WO2008/128522
PCT Pub. Date: Oct. 30, 2008

(65) Prior Publication Data
US 2011/0129885 A1  Jun. 2, 2011

(30) Foreign Application Priority Data
Apr. 20, 2007 (DE) .......................... 10 2007 019 184

(51) Int. Cl.
C12N 1/00 (2006.01)
(52) U.S. Cl.
USPC ..................................................... 435/254.2
(58) Field of Classification Search
None
See application file for complete search history.

(56) References Cited

U.S. PATENT DOCUMENTS

| | | | |
|---|---|---|---|
| 5,143,834 A | 9/1992 | Glassner et al. | |
| 5,869,301 A | 2/1999 | Nghiem et al. | |
| 6,190,914 B1 | 2/2001 | Grivell et al. | |
| 7,063,968 B2 | 6/2006 | Lee et al. | |

FOREIGN PATENT DOCUMENTS

| | | |
|---|---|---|
| EP | 1672077 A1 | 6/2006 |
| WO | 2006034156 A2 | 3/2006 |

OTHER PUBLICATIONS

Przybyla-Zawislak et al. "Genetic and Biochemical Interactions Involving Tricarboxylic Acid Cycle (TCA) Function Using a Collection of Mutants Defective in All TCA Cycle Genes", Genetics 152: 153-166 (May 1999).
Kuangyu Yen et al., Abstract from "An improved tetO promoter replacement system for regulating the expression of yeast genes" (Yeast, vol. 20, Issue 15 , pp. 1255-1262, Published Online: Oct. 16, 2003), obtained from Wiley InterScience website at: http://www3.interscience.wiley.com/journal/106559095/abstract.
Minard et al.: "Glucose-Induced Degradation of the MDH2 Isozyme of Malate Dehydrogenase in Yeast", Journal of Biological Chemistry, vol. 267, No. 24, 1992, pp. 17458-17464.
Sanchez et al.: "Efficient succinic acid production from glucose through overexpression of pyruvate carboxylase in an *Escherichia coli* alcohol dehydrogenase and lactate dehydrogenase mutant", Biotechnology Progress, XX, XX, vol. 21, No. 2, Mar. 2, 2005, pp. 358-365.
Arikawa et al.: "Effect of gene disruptions of the TCA cycle on production of succinic acid in *Saccharomyces cerevisiae*", Journal of Bioscience and Bioengineering, Elsevier, Amsterdam, NL, vol. 87, No. 1, Jan. 1, 1999, pp. 28-36.
Blom et al.: "Redirection of the respiro-fermentative flux distribution in *Saccharomyces cerevisiae* by overexpression of the transcription factor Hap4p", Applied and Environmental Microbiology, vol. 66, No. 5, May 2000, pp. 1970-1973.
Cui et al (2004). "The type 1 phosphatase Reg1p-Glc7p is required for the glucoseinduced degradation of fructose-1,6-bisphosphatase in the vacuole." J Biol Chem 279(11): 9713-24.
De Vit et al. (1997). "Regulated nuclear translocation of the Mig1 glucose repressor." Mol Biol Cell 8(8): 1603-18.
Frederick et al. (1996). "The REG2 gene of *Saccharomyces cerevisiae* encodes a type 1 protein phosphatase-binding protein that functions with Reg1p and the Snf1 protein kinase to regulate growth." Mol Cell Biol 16 (6): 2922-31.
Gancedo (1998). "Yeast carbon catabolite repression." Microbiol Mol Biol Rev 62(2): 334-61.
Haurie et al. (2001). "The transcriptional activator Cat8p provides a major contribution to the reprogramming of carbon metabolism during the diauxic shift in *Saccharomyces cerevisiae*." J Biol Chern 276(1): 76-85.
Hung et al. (2004). "Degradation of the gluconeogenic enzymes fructose-1,6-bisphosphatase and malate dehydrogenase is mediated by distinct proteolytic pathways and signaling events." J Biol Chern 279(47): 49138-50.
Jiang et al. (1997). "The Snf1 protein kinase and its activating subunit, Snf4, interact with distinct domains of the Sip1/Sip2/Gal83 component in the kinase complex." Mol Cell Biol 17(4): 2099-106.
Lascaris et al. (2004). "Overexpression of HAP4 in glucose-derepressed yeast cells reveals respiratory control of glucose-regulated genes." Microbiology 150(Pt 4): 929-34.
Lopez-Boado et al. (1988). "Glucose-stimulated phosphorylation of yeast isocitrate lyase in vivo." J Gen Microbiol 134(9): 2499-505.
McNabb et al. (2005). "Assembly of the Hap2p/Hap3p/Hap4p/Hap5p-DNA complex in *Saccharomyces cerevisiae*." Eukaryot Cell 4(11): 1829-39.

(Continued)

*Primary Examiner* — Anand Desai
(74) *Attorney, Agent, or Firm* — Mayer & Williams PC; Ann Wieczorek (57) ABSTRACT

The invention relates to an isolated genetically modified microorganism in which the gene IDH1 and at least one of the genes SDH2 and DIC1 are under the control of a first promoter that is repressed to a growth culture medium by means of a cultivation additive and is active in the absence of the cultivation additive. The genes that are part of the group comprising "PYC1, ACS1, CIT1, ACO1, ICL1, MSL1, and CIT2, optionally also MDH3" are constitutively active. The invention further relates to uses of such a microorganism, especially for producing succinic acid.

6 Claims, 3 Drawing Sheets (56) References Cited

OTHER PUBLICATIONS

Ordiz et al. (1996). "Glucose-induced inactivation of isocitrate lyase in *Saccharomyces cerevisiae* is mediated by the cAMP-dependent protein kinase catalytic subunits Tpk1 and Tpk2." FEBS Lett 385(1-2): 43-6.

Rubenstein et al. (2006). "Regulatory domains of Snf1-activating kinases determine pathway specificity." Eukaryot Cell 5(4): 620-7.

Santangelo (2006). "Glucose signaling in *Saccharomyces cerevisiae*." Microbiol Mol Biol Rev 70(1): 253-82.

Sass et al. (2003). "Folding of fumarase during mitochondrial import determines its dual targeting in yeast." J Biol Chem 278(46): 45109-16.

Schuller et al. (1991). "Extragenic suppressors of yeast glucose derepression mutants leading to constitutive synthesis of several glucose-repressible enzymes." J Bacteriol 173(6): 2045-52.

Treitel et al. (1995). "Repression by SSN6- TUP1 is directed by MIGI, a repressor/activator protein." Proc Natl Acad Sci USA 92(8): 3132-6.

Treitel et al. (1998). "Snf1 protein kinase regulates phosphorylation of the Mig1 repressor in *Saccharomyces cerevisiae*." Mol Cell Biol 18(11): 6273-80.

Young et al. (2003). "Multiple pathways are co-regulated by the protein kinase Snf1 and the transcription factors Adr1 and Cat8." J Biol Chem 278(28): 26146-58. 1m.

Guldener et al, "A new efficient gene disruption cassette for repeated use in budding yeast", Nucleic Acids Research, 1996, vol. 24, No. 13, pp. 2519-2524.

Yen et al., "An improved tetO promoter replacement system for regulating the expression of yeast genes", Yeast 2003; 20; pp. 1255-1262.

De Risi et al., "Exploring the Metabolic and Genetic Control of Gene Expression on a Genomic Scale", Science (1997), vol. 278, pp. 680-686.

Lang et al., "Efficient expression and secretion of *Aspergillus niger* RH5344 polygalacturonase in *Saccharomyces cerevisiae*", Appl Microbiol Biotechnol (1995); 44; pp. 147-156.

Gari et al., "A Set of Vectors with a Tetracycline-Regulatable Promoter System for Modulated Gene Expression in *Saccharomyces cerevisiae*", Yeast (1997) vol. 13, pp. 837-848.

Manivasakam et al., "High efficiency transformation of *Saccharomyces cerevisiae* by electroporation", Nucleic Acids Research, 1993, vol. 21, No. 18, pp. 4414-4415.

Naumovski et al., "Molecular Cloning of Eucaryotic Genes Required for Excision Repair of UV-Irradiated DNA: Isolation and Partial Characterization of the RAD3 Gene of *Saccharomyces cerevisiae*", Journal of Bacteriology, Oct. 1982, pp. 323-331.

Skorski et al., "A System of Shuttle Vectors and Yeast Host Strains Designed for Efficient Manipulation of DNA in *Saccharomyces ceratisiae*", Genetics 122 (1989), pp. 19-27.

Growth Phase

Figure 1

Production Phase (e.g. succinic acid)

MICROORGANISM FOR THE PRODUCTION OF SUCCINIC ACID

FIELD OF THE INVENTION

The invention relates to a microorganism comprising the gene IDH1 and at least one of the genes SDH2 and/or DIC1, to the uses of such a microorganism and to a method for the production thereof.

PRIOR ART AND BACKGROUND OF THE INVENTION

Dicarboxylic acids have a high economic potential, since they can be used as precursor substances for numerous chemicals. For instance, succinic acid serves as a preliminary stage for the production of plastics based on 1,4-butanediol, tetrahydrofuran and gamma-butyrolactone. Today, succinic acid is produced chemically by catalytic hydration of maleic acid anhydride to succinic acid anhydride and subsequent water addition or by direct catalytic hydration of maleic acid.

Succinic acid is also formed by many microorganisms from sugars or amino acids under physiological environmental conditions. Under anaerobic conditions, normally further fermentation end products such as ethanol, lactic acid, acetic acid and formic acid are formed, beside succinic acid. The biosynthesis of succinic acid with its high oxygen content requires a reductive $CO_2$ fixation.

Succinic acid is a metabolite, which is normally enriched by anaerobic fermentation processes. Whereas the yield and enrichment of the product under anaerobic conditions is manifold better than under aerobic conditions, the drawback of an exclusively anaerobic process is the technical limitation of the biomass production and a low productivity of the microbial producer. Thus, the consequence is a relatively low biomass/product efficiency. Further, it is difficult to technically handle strictly anaerobic microorganisms.

Various microorganisms that are capable to synthesize succinic acid under anaerobic conditions are known in the art. Document U.S. Pat. No. 5,143,834 describes a variant of *A. succiniciproducens*. This is an obligate anaerobic microorganism, which can produce moderate amounts of succinic acid only, and is further not capable to tolerate high osmotic pressures and salt concentrations. Document U.S. Pat. No. 7,063,968 describes a microbial rumen isolate, *Mannheimia* sp. 55E, which is capable to synthesize organic acids under aerobic as well as anaerobic conditions. This is however not a specific enrichment of succinic acid, but a mixture of different organic acids, such as formic acid, acetic acid, lactic acid, and succinic acid. The drawback of this producer is that an economic use of the strain is only difficultly possible, if not impossible, since for obtaining succinic acid, expensive enrichment and purification methods have to be employed. Document U.S. Pat. No. 5,869,301 describes a method for the production of dicarboxylic acids in a two-step fermentation process with *E. coli* AFP-111, wherein in the first phase microbial biomass is produced under aerobic conditions, and in a second phase the production of succinic acid is carried out in an anaerobic manner. The first phase of biomass generation is limited in this process, since the glucose concentration in the fed-batch process must be limited to 1 g/L, in order to avoid an enrichment of acetate, which disturbs the biomass production process as well as the succinic acid production. Thus, the biomass generation by this process is possible to a limited degree only. Further, the biosynthesis pathway for the succinic acid in this process is subject to a strong catabolite repression, since genes of the glycolysis, of the citric acid cycle and of the glyoxylate pathway are strongly repressed by glucose, as is known from the document DeRisi J. L., Iyer V. R., Brown P. O., Science 278 (5338): 680-686 (1997). The consequence is that the synthesis of succinic acid in presence of glucose is to a great extent repressed and thus strongly limited.

From document U.S. Pat. No. 6,190,914, microorganisms are known in the art, wherein by modulation of suitable transcription factors and kinases the glucose repression of various genes is reduced. The production of organic acids by means of such microorganisms, in particular also further for the production of microorganisms optimized to organic acids, cannot be found therein.

TECHNICAL OBJECT OF THE INVENTION

It is therefore the technical object of the invention to specify a method and a microorganism for carrying out the latter, which permits to produce biomass without limitations in the fermentation process, to produce a carboxylic acid of the glyoxylate cycle, in particular succinic acid, without catabolite repression in the biosynthesis pathway in the production process, and to secure an as low side product enrichment as possible during the production phase.

BASICS OF THE INVENTION AND PREFERRED EMBODIMENTS

For achieving this technical object, the invention teaches an isolated genetically modified microorganism, wherein the gene IDH1 and at least one of the genes DIC1 and SDH2 or both of these genes are under the control of a first foreign promotor that is repressed to a growth culture medium by means of a cultivation additive and is active in the absence of the cultivation additive, and the use of such a microorganism in a method for the production of a carboxylic acid of the glyoxylate cycle, in particular of a dicarboxylic acid, for instance succinic acid, comprising the following steps: a) the microorganism is cultivated and multiplied in the growth culture medium, b) then the microorganism is transferred into a production culture medium, which contains the cultivation additive repressing the first promotor, or the cultivation additive repressing the first promotor is added to the growth culture medium and cultivated (if applicable under aerobic or anaerobic conditions), and c) after step b) or during step b), the carboxylic acid is separated from the culture supernatant and optionally is purified.

Further, by the microorganism or the method according to the invention, by suitable gene repression, various intermediates of the glyoxylate or citrate cycle can specifically be produced as final products of the production method. When the genes IDH1, SDH2 and DIC1 are under the control of the first foreign promotor, the generated carboxylic acid is succinic acid (succinate). When the genes SDH2 and DIC1 are not under the control of the first foreign promotor, and the genes IDH1, FUM1 and OSM1 are under the control of the first foreign promotor, the generated carboxylic acid is fumaric acid (fumarate). When the genes FUM1 and OSM1 are not under the control of the first foreign promotor, and the genes IDH1 and MDH3 are under the control of the first foreign promotor, the generated carboxylic acid is maleic acid (malate). When the gene MDH3 is not under the control of the first foreign promotor, and the genes IDH1 and CIT2 are under the control of the first foreign promotor, the generated carboxylic acid is oxalacetic acid (oxalacetate).

The invention uses the following findings and achieves the following advantages.

During the cell respiration, reduction equivalents are obtained from the citrate cycle, wherein succinic acid is an intermediate, said reduction equivalents leading to the generation of a potential within the mitochondrial membrane system. This membrane potential serves then in the course of the respiration chain for energy generation in the form of ATP. Further, carbon is efficiently transformed by the citrate cycle in anabolic processes into biomass. This form of energization is very efficient and leads to an optimum growth of the cells. It is however only possible, as long as the citrate cycle and the respiration chain occur in the mitochondrial membrane. Beside the citrate cycle, the glyoxylate metabolic pathway occurs in the yeast *Saccharomyces cerevisiae* (see also FIG. 1). It is kind of a "short-circuit" of the citrate cycle, since isocitrate is removed from the metabolic pathway as a metabolite, and one molecule succinic acid and glyoxylate each are formed. As long as the citrate cycle is active, succinic acid and glyoxylate will flow back into the citrate cycle by that a molecule acetyl-CoA (of ethanol or acetate) is bound to glyoxylate and malate is generated therefrom. The glyoxylate cycle allows the cell to supply without losses of carbon $C_2$ carbon sources by acetyl-CoA into the citrate cycle, since the two oxidative decarboxyling steps from isocitrate to succinyl-CoA are bypassed.

Naturally, the glyoxylate cycle, for instance in a yeast cell, is transcriptionally strongly repressed in the presence of glucose, and the consequence is that this metabolic pathway is not active. Only when the glucose is completely used up, and ethanol is enriched in the culture medium, the involved genes are transcriptionally derepressed. This form of regulation is explained by the biological meaning of the glyoxylate metabolic pathway, namely the refilling or metabolization of C2 carbon compounds, such as ethanol or acetate, in order to compensate the carbon loss by generation of these C2 carbon compounds during the glycolytic decomposition. The biosynthesis pathway is in particular found in plants, fungi and yeasts.

An enrichment of succinic acid during the respiration phase (aerobic phase) and thus the phase, wherein the microorganism obtains biomass, makes no sense, since the carbon is fully needed for anabolic processes. If however the biomass increase in the stationary phase is terminated by limitation of medium components, the citrate cycle is not required by the cell anymore. This time can be taken to effect a specific enrichment of succinic acid by the culture by that the carbon flux is deflected into the glyoxylate cycle and thus efficiently into the succinic acid synthesis.

In order to achieve this metabolic deflection of the carbon flux, the citrate cycle is interrupted after the intermediates isocitrate and succinate, such that the carbon flux is deflected into the glyoxylate cycle, and the further metabolization of succinate is prevented or rerouted to further intermediates of the glyoxylate cycle. Further, the transportation of the succinate from the glyoxylate cycle into the mitochondrion is interrupted, such that it is not available anymore for the citrate cycle localized in the mitochondrion. Further, the natural regulatory mechanism of the cell must be overcome, since for an efficient carbon exploitation in succinic acid by the glyoxylate pathway, glucose, which naturally represses the metabolic pathway, is used as the carbon source.

Figure 1:
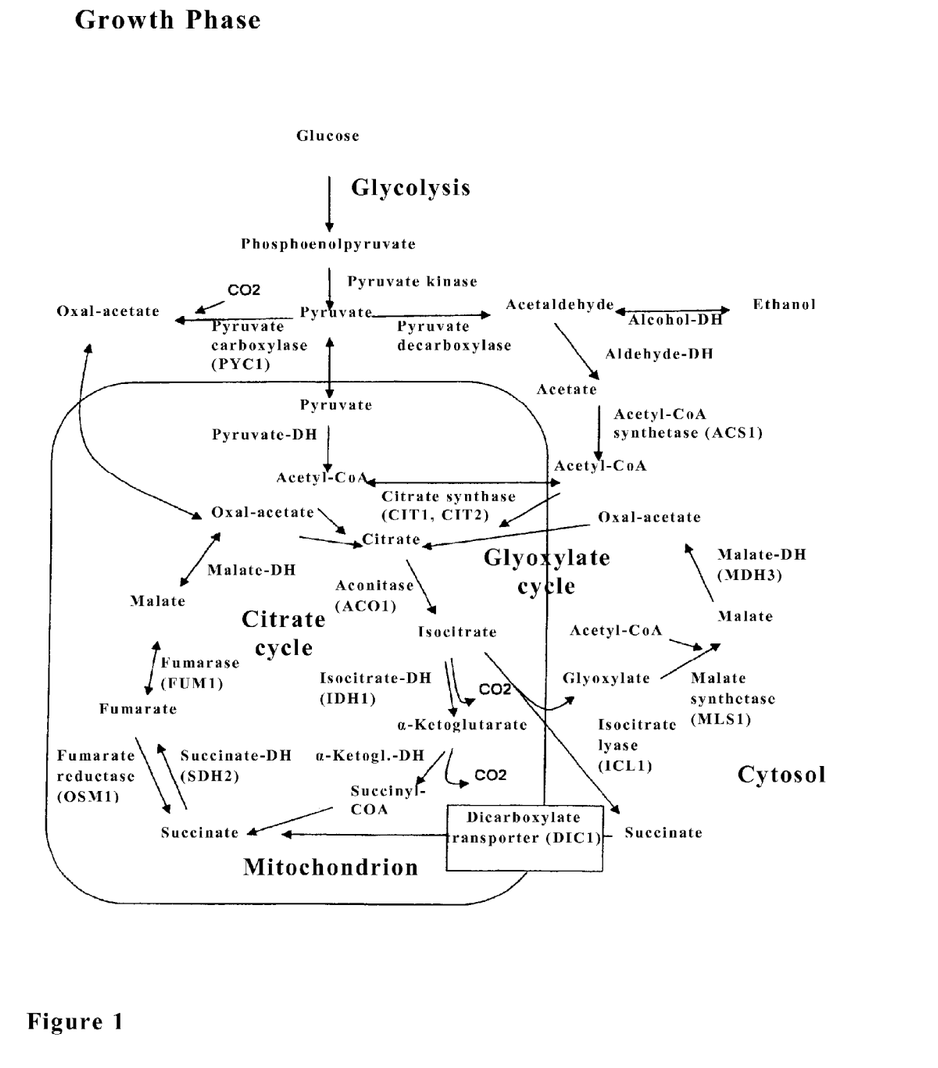
FIG. 1 shows a diagram of the pathway for the growth phase of cells.
Figure 2:
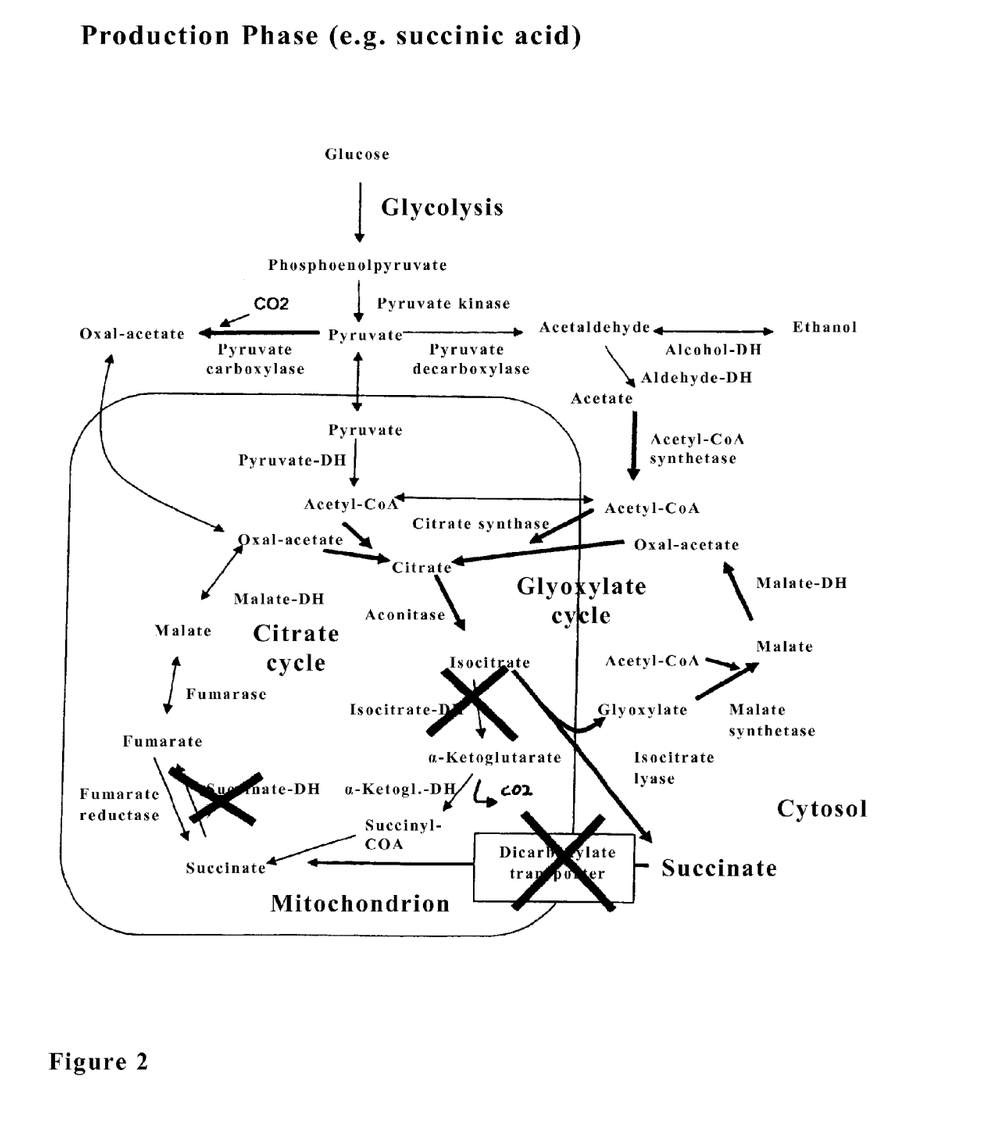
FIG. 2 shows a diagram of the pathway for the production of succinic acid.

For a process, wherein initially in a first growth phase biomass is to be enriched, and in a second phase succinic acid is to be efficiently produced and transferred into the culture medium, a microorganism must be modified by molecular-genetic methods such that the citrate cycle is interrupted after the growth phase, and the glyoxylate cycle is activated in the presence of glucose, i.e. is derepressed. If such a modified microorganism does not depend anymore on the increase of biomass, the carbon flux of glucose can highly efficiently occur into a carboxylic acid or succinic acid. The metabolic situation in such a strain is shown in FIG. 2. For comparison purposes, the metabolic situation of a wild-type strain is shown in FIG. 1.

The method according to the invention and the microorganism according to the invention that can be used in such a method meet these requirements. It is a microorganism being modified genetically or by genetic mutation and a corresponding fermentation method, wherein initially during a first phase (respiration phase) an optimum increase of biomass of the microbial producer is secured and then in a second phase (production phase) the enrichment of carboxylic acids, for instance succinic acid, from primary carbon sources (e.g. glucose) and $CO_2$ (anaplerotic reaction, $CO_2$ fixation) follows. During the production phase, by genetic modification of the microorganism, the citrate cycle is interrupted after the intermediates isocitrate and succinate, and the transportation of the succinate from the glyoxylate cycle is prevented, as described above. Further, during the production phase, the catabolite repression is disabled, with the consequence that even in the presence of C6 carbon molecules the efficient biosynthesis and enrichment of carboxylic acids or succinic acid occurs in the culture supernatant. The control of the metabolic processes in the various steps takes place by addition or non-addition or removal of the cultivation additive, which represses the first promotor, or the presence of which is necessary for the activity of the first promotor.

It is therefore also preferred that the cultivation additive is not endogenous in the organism. Then, a very simple control process of the first promotor and thus of the genes regulated by the promotor can be carried out by addition of the cultivation additive to the culture medium or the non-addition or separation thereof. The cultivation additive may for instance be an antibiotic from the group of the tetracyclines, in particular tetracycline.

The promotor is preferably selected from the group comprising "$tetO_2$ and $tetO_7$". The employed promotor is in particular the $tetO_7$ promotor, which forms, together with a second component, the transcriptional transactivator (tTA), a promotor system that is described in the document Gari E. et al., YEAST 13:837-848 (1997). By using this promotor, no cultivation additive is added to the medium during the growth phase for the biomass enrichment, and the respiratory metabolism works normally. If at the end of the growth phase, the cultivation additive is added, the promotor and thus the gene expression is repressed, and the carbon cannot be metabolized anymore by the citrate cycle and is therefore completely available for the glyoxylate pathway and the efficient carboxylic acid or succinic acid production.

Preferably, the microorganism is a yeast cell, for instance the yeast *Saccharomyces cerevisiae*. The use of yeast for the production process offers the following advantages, compared to established methods: yeast is very tolerant to organic acids and ethanol, yeast is very osmotolerant, yeast can be cultivated in relatively short times to large amounts of biomass, yeast has a glyoxylate biosynthesis pathway for the loss-free use of carbon during the biomass generation and for the loss-free use of carbon for the carboxylic acid or succinic acid production, and yeast can easily be modified molecular-biologically in a complex way by simple, very well established genetic tools. Further, yeast is a robust and proven production organism on an industrial scale (see also bioethanol production) and does not cause a mixed acid fermentation, such as for instance *E. coli* or *A. Succinogenes*. Beside the carboxylic acids, therefore, practically no further fermentation end products are generated, beside ethanol that can easily be separated.

For improving the efficiency and the yield, it is recommended to delete or inactivate the wild-type gene IDH1, SDH2 and/or DIC1, for instance by exchange of the native promotor of these genes by a repressible promotor system. Thereby it is secured that these genes are not active in the production phase, step b), which would affect the production of carboxylic acids or succinic acid for the above reasons.

Further it is preferred for improving the yield and increasing the production that one or more different or all of the genes from the group "PYC1, ACS1, CIT1, ACO1, ICL1, MLS1, MDH3, and CIT2" are included and are under the control of a constitutively active second promotor. Preferably, this is the ADH1 promotor.

A microorganism according to the invention is particularly well suited for the production of succinic acid.

For the method according to the invention, it is preferred that step a) is carried out up to a cell density of at least 100 g dry biomass/l, preferably at least 120 g/l, most preferably at least 140 g/l. Step b) can be carried out up to a carboxylic acid concentration of at least 0.4 mol/l, preferably at least 0.8 mol/l, most preferably at least 1.0 mol/l. In step a), a pH in the range from 4 to 9, preferably 6 to 8, and a salt concentration in the range from 0.01 to 0.5 mol/l, preferably at least from 0.05 to 0.2 mol/l, most preferably from 0.05 to 0.1 mol/l can be adjusted. In step b), a pH in the range from 4 to 9, preferably 6 to 8, and a salt concentration in the range from 0.01 to 0.5 mol/l, preferably at least from 0.05 to 0.2 mol/l, most preferably from 0.05 to 0.1 mol/l can be adjusted. Step a) is preferably carried out at a temperature from 20 to 35° C., preferably from 28 to 30° C., and for a time from 1 to 1,000 h, preferably from 2 to 500 h, most preferably from 2 to 200 h. In step b), a temperature from 15 to 40° C., preferably from 20 to 35° C., most preferably from 28 to 30° C., and a time from 1 to 1,000 h, preferably from 2 to 500 h, most preferably from 2 to 200 h are preferred.

As a culture medium for step a), for instance WMVIII medium (Lang C., Looman A. C., Appl. Microbiol. Biotechnol. 44(1-2): 147-156 (1995)) can be used. The amount of tetracycline in the culture medium is less than 20 mg/l, preferably less than 10 mg/l, most preferably less than 1 mg/l, down to values that are below the detection limit.

As a culture medium for step b), for instance WMVIII medium can be used, but usual molasses medium can also be employed. The amount of tetracycline preferably is more than 1 mg/l, most preferably more than 3 mg/l. As ranges can be used 1 to 3 mg/l or 3 to 15 mg/l.

Step c) can be carried out after step b). Then, the culture supernatant is separated from the microorganisms, for instance by filtration or centrifugation. Step c) can however also be carried out during step b), continuously or discontinuously. In the latter case, at least part of the culture supernatant is removed and replaced by new culture medium, and this process is repeated, if applicable several times. From the removed culture supernatant, the succinic acid is obtained. A continuous separation can be carried out by suitable membranes or by conducting the flux of the culture medium through a device for separating the succinic acid.

Finally, the invention relates to a method for the production of a microorganism according to the invention, wherein in the wild-type microorganism or in a microorganism genetically modified or mutated compared to the wild-type, the wild-type gene IDH1, SDH2 and/or DIC1 is deleted or inactivated, and wherein this gene or these genes are under the control of a first promotor, which is repressed by a cultivation additive to a growth culture medium and is active in the absence of the cultivation additive. This promotor and the tTA belonging to the tetracycline-regulated promotor system are introduced into the microorganism, and the microorganism is transformed therewith.

Preferably, one or more different or all of the genes from the group "PYC1, ACS1, CIT1, ACO1, ICL1, MLS1, MDH3, and CIT2" are introduced under the control of a constitutively active second promotor into the microorganism, and the microorganism is transformed therewith. The first promotor may in particular be the $tetO_7$ promotor, and the second promotor may be the ADH1 promotor.

The genes and promotors used for the purpose of the invention, or the nucleic acid sequences thereof are described with the following Accession Nos. of the NCBI database or in the following documents:

IDH1: Z71313 Y13139
SDH2: Z73146 Y13138
DIC1: EF059331
FUM1: NC001148
OSM1: NC001142
PYC1: Z72584 Y13135
ACS1: AY723758
IT1: Z71616 Y13139
ACO1: M33131
ICL1: X65554
MLS1: X64407 S50520
MDH3: M98763
CIT2: Z11113
tetO and tTA: Gari E. et al., YEAST 13:837-848 (1997)
ADH1: Lang C., Looman A. C., Appl Microbiol Biotechnol. 44 (1-2): 147-156 (1995)

The transformation of yeast cells can be made in a conventional way and with respect thereto reference is made to the documents Schiestl R. H. et al., Curr Genet. December, 16(5-6):339-346 (1989), or Manivasakam P. et al., Nucleic Acids Res. September 11, 21(18):4414-4415 (1993), or Morgan A. J., Experientia Suppl., 46:155-166 (1983).

Vehicles suitable for the transformation, in particular plasmids, are for instance known from the documents Naumovski L. et al., J Bacteriol, 152(1):323-331 (1982), Broach J. R. et al., Gene, 8(1):121-133 (1979), Sikorski R. S. et al., Genetics, 122(1) 19-27 (1989). These vectors are Yep24, Yep13, pRS-vector series, and YCp19 or pYEXBX.

The production of expression cassettes suitable for the purpose of the invention typically takes place by fusion of the promotor with the nucleic acid sequence encoding for the gene and if applicable a terminator according to usual recombination and cloning techniques, such as described for instance in the documents Maniatis T. et al., Molecular Cloning: A Laboratory Manual, Cold Spring Harbor Laboratory, Cold Spring Harbor, N.Y., USA, 1989, or Sihlavy T. J., at al., Experiments with Gene Fusions, Cold Spring Harbor Laboratory, Cold Spring Harbor, N.Y., USA, 1984, or Ausubel F. M. et al., Current Protocols in Molecular Biology, Greene Publishing Assoc. and Wiley-Interscience, 1987.

In the following, alternatives and/or improvements of the invention of independent significance are described. Suitable ones of the above explanations and variants can also be used in an analogous manner in the alternatives and/or improvements described in the following, and vice versa.

The improvement comprises in all alternatives the influence of kinases and transcription factors of the glucose repression cascade. The alternatives comprise the use of the reductive citrate cycle for increasing the efficiency of the production of organic acids of the respiratory central metabolism in yeasts, for instance with the yeast *Saccharomyces cerevisiae*.

In the following, an optimized method for the production of succinic acid and other organic acids of the respiratory central metabolism is described by means of a yeast strain, in particular of a *Saccharomyces cerevisiae* yeast strain that has a reduced glucose repression.

The reduced glucose repression is achieved by specific influence of suitable transcription factors and kinases, which are responsible for the glucose repression, in "Crabtree"-positive yeasts. In this way, the efficiency of the production of organic carboxylic acids, in particular dicarboxylic acids and hydroxy fatty acids of the respiratory central metabolism of the yeast, such as for instance succinic acid, fumaric acid, malic acid, oxalacetic acid is improved with regard to production time and yields.

Figure 3:
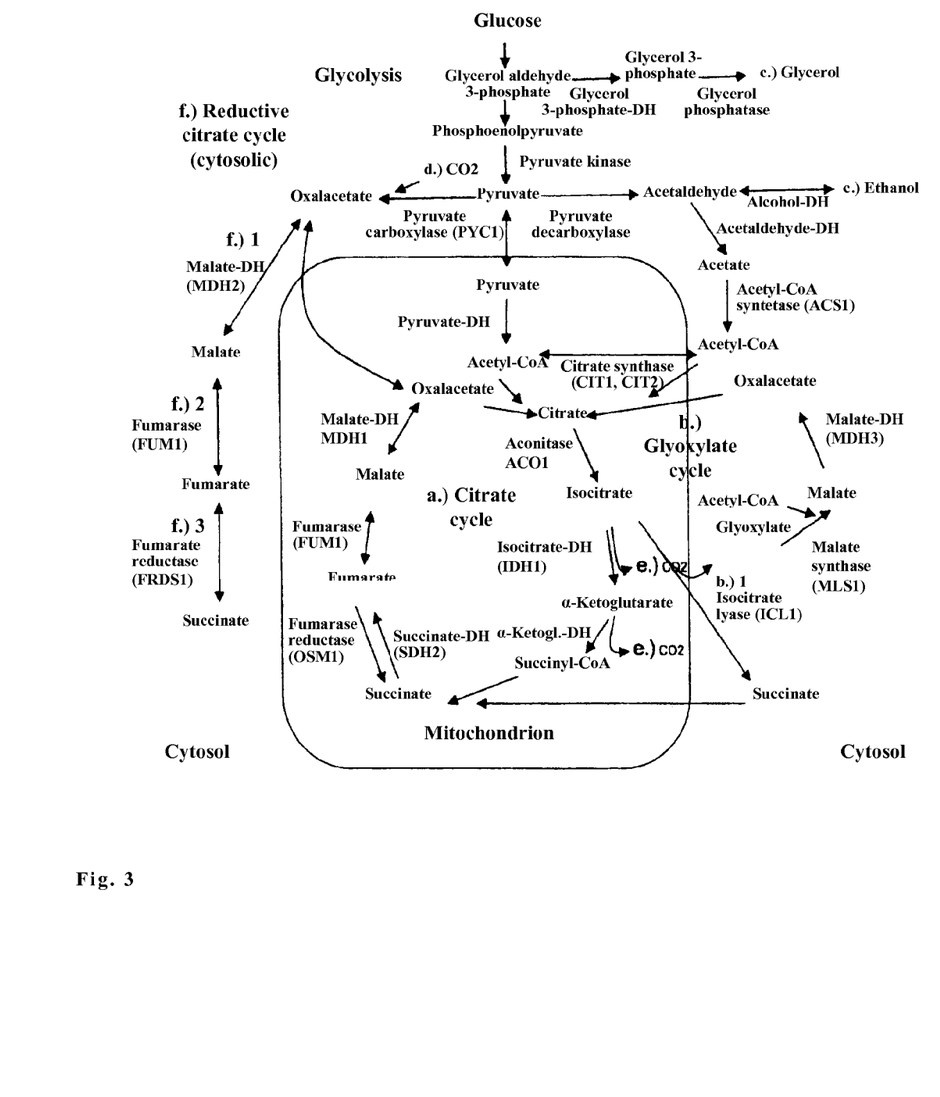
FIG. 3 shows a diagram of the pathway for the production of succinate by the reductive citrate cycle.

During cellular respiration, starting from the substrate, e.g. glucose, carbon is not transformed into ethanol or glycerol, as during the fermentation, but enters the respiratory central metabolism, i.e. the citrate cycle or the glyoxylate cycle (see FIG. 3a.), b.) and c.)). When the carbon passes these two cycles, redox equivalents in the form of NADH or NADPH are formed, the electrons of which are transferred to the first protein complex of the respiratory chain, which is localized in the inner mitochondrial membrane. These electrons will then transfer oxygen step by step by further protein complexes of the respiratory chain to the final electron acceptor, said oxygen being then reduced to water. The released energy of this controlled oxyhydrogen reaction is used for transporting protons against a gradient into the intermembrane space of the mitochondria, which then when flowing back into the mitochondrion will drive the so-called "proton pump" by the complex V of the respiratory chain, whereby energy in the form of ATP is generated.

Under fermentation conditions, the yeast produces, beside glycerol, mainly ethanol (see FIG. 3c.)) and generates per molecule glucose only 2 energy equivalents in the form of ATP, compared to the respiration, wherein per molecule glucose 38 ATP can be generated. During the fermentation, NADH is reoxidized to NAD by the synthesis of ethanol or glycerol and not, as during the respiration, by the delivery of the electrons on oxygen, since under anaerobic conditions oxygen is not available as a final electron acceptor. Under fermentation conditions only very little carbon undergoes the respiratory central metabolism, so that intermediates of the citrate cycle are still available as precursor molecules for the synthesis of amino acids being necessary for growth.

The yeast *Saccharomyces cerevisiae* is "Crabtree"-positive. This means that the yeast ferments on primary carbon sources, as for instance glucose, even under aerobic conditions, and does not respire. This fermentation activity can be observed starting from a glucose concentration of about 100 mg/l glucose already in the culture medium, since at this concentration the limit of the respiratory capacity of the yeast cell is achieved. The reason of this is that in the presence of glucose a plurality of the genes of the respiratory central metabolism, i.e. of the citrate and glyoxylate cycle (see FIG. 3a.) and b.)) and of the respiratory chain are transcriptionally strongly repressed (Gancedo 1998). This phenomenon is also called glucose or catabolite repression. The mechanisms, which are responsible for the glucose repression, are not yet fully clarified. It is however known that a plurality of activating and repressing transcription factors and kinases are responsible for the glucose repression cascade.

Furthermore, all genes that are responsible for the metabolization of alternative carbon sources are also strongly repressed in the presence of glucose, so that the yeast will always first exploit glucose as a substrate, that is why it also called "glucophilic" (Gancedo 1998). Only when all glucose is used up, the genes for the metabolization of alternative carbon sources, the genes of the respiratory metabolism and the respiratory chain, and of the oxidative stress response are expressed (Haurie et al. 2001). This profound modification of the transcriptional expression profile, when the glucose in the medium is used up, is called "diauxic shift". During the "diauxic shift", there is a shift of the respiro-fermentative balance in the direction of respiration. The yeast cell changes from fermentation to respiration, and can now metabolize the ethanol generated during the fermentation by the respiratory metabolism. The "diauxic shift" only occurs, if the catabolite repression in the course of the glucose consumption is suspended. A yeast strain that in spite of the presence of glucose does not show any or a reduced glucose repression is far better suitable for the production of dicarboxylic acids, such as succinic acid, fumaric acid, malic acid and oxalacetic acid on primary carbon sources, than a wild-type strain, since these acids are intermediates of the citrate and glyoxylate cycle, the genes of which are subject to this repression. A reduced glucose repression leads to a shift of the respiro-fermentative balance in the direction of respiration, which has as a consequence the propagation of the complete respiratory system and the increase of the carbon flux by the central metabolism in the direction of the desired organic acid.

Under respiratory conditions, further the glyoxylate cycle (see FIG. 3b.)) is propagated. The biological significance of the glyoxylate metabolic pathway is the refilling or metabolization of C2-carbon compounds, such as ethanol and acetate, which can be fed by the glyoxylate cycle without carbon losses into the metabolism, whereby a growth on C2-compounds will only become possible. During the production of organic acids by the glyoxylate cycle there is the advantage that the two oxidative decarboxylation steps of isocitrate to succinyl-CoA in the citrate cycle, and thus the loss of carbon in the form of two times $CO_2$ (see FIG. 3e.)) can be bypassed.

The deflection of the carbon flux into the glyoxylate cycle thus essentially contributes to the increase of the yield during the production of organic acids in yeast. Ultimately, the carbon of the $CO_2$ released in the citrate cycle originates from the corresponding substrate e.g. glucose or from the $CO_2$ fixation (anaplerotic reaction). Various enzymes of the citrate and glyoxylate cycle, the genes of which are transcriptionally repressed by glucose, are subject also on the protein level to the regulation or inactivation by glucose. A transcriptional deregulation of these genes is thus not sufficient for obtaining an active gene product. Inactivation effects on the protein level must also be bypassed, which can be obtained by a reduced glucose repression.

An example is one of the main enzymes of the glyoxylate cycle, the isocitrate lyase (Icl1p, FIG. 3b.) 1). This enzyme, which is essential for the efficient production of organic acids, is subject in the presence of glucose to the inactivation by phosphorylation and an increased proteolytic degradation (Lopez-Boado et al. 1988; Ordiz et al. 1996).

In the following, alternative, but also arbitrarily combinable features of an alternative of the invention according to the claims are explained. The cytosolic malate dehydrogenase (Mdh2p), too, is subject to an increased proteolytic degradation induced by glucose (Hung et al. 2004). The cytosolic malate dehydrogenase is used for the succinate synthesis by the reductive part of the citrate cycle, starting from pyruvate and oxalacetate, malate and fumarate to succinate (FIG. 3f.) 1). The reductive citrate cycle, i.e. the non-cyclic return part of the citrate cycle (FIG. 3f.) is the prerequisite for the stoichiometrically maximum molar yield during the production of succinic acid on glucose. Only the reductive citrate cycle in combination with the glyoxylate cycle permits during the production of succinic acid maximum yields of up to 1.71 mol succinate per mol glucose by reoxidation of NADH to NAD+ and $CO_2$ fixation.

Another possibility to deprive the cytosolic malate dehydrogenase (Mdh2p) of the glucose-induced proteolytic degradation is the overexpression of an Mdh2p protein shortened by the first 12 N-terminal amino acids, and, optionally, of the C-terminal proline. The first 12 N-terminal amino acids, and the C-terminal proline are essential for the degradation of Mdh2p (Hung, Brown et al. 2004).

Another bottleneck for the succinate production by the reductive part of the citrate cycle is the reaction of malate to fumarate (FIG. 3f.) 2). This reaction is catalyzed by the enzyme fumarase (Fum1p). It is one of the few enzymes of the respiratory central metabolism, which has no isoenzymes. Nevertheless, it is localized in the cytosol, as well as in the mitochondrion. The localization of the singular translation product is determined by the N-terminal mitochondrial targeting sequence and the protein folding (Sass et al. 2003).

The reaction of malate to fumarate is thermodynamically very unfavorable, since the fumarase has a 17 times higher affinity to fumarate than to malate. Therefore, an efficient use of the reductive part of the citrate cycle for the production of succinate is not possible with the native fumarase of the yeast *Saccharomyces cerevisiae*.

In order to overcome these problems, a fumarase enzyme must heterologously be expressed in the yeast, which enzyme preferably originates from an organism, which naturally carries out a mixed acidic fermentation. In these organisms, the reductive citrate cycle is much more efficient, since in the mixed acidic fermentation, succinate is a natural fermentation end product. The thermodynamics of the fumarase of such organisms is much more favorable with respect to the reaction of malate to fumarate than in *Saccharomyces cerevisiae*. As donor organisms for a heterologously expressed fumarase, for instance *Escherichia coli, Anaerobiospirillum succiniciproducens, Actinobacillus succinogenes, Mannheimia succiniciproducens, Corynebacterium glutamicum* can be used.

The last step for the succinate production by the reductive citrate cycle is the reaction of fumarate to succinate. This reaction is catalyzed in the cytosol by the enzyme fumarate reductase (Frds1p, FIG. 3f.) 3). An overexpression of this enzyme increases the efficiency of the reductive succinate production.

Therefore, the invention also teaches an isolated genetically modified microorganism, wherein a truncated variant of the natural gene MDH2 is introduced into the microorganism, and/or the natural gene FUM1 is replaced by the gene FUM1 from an organism being different from the microorganism, and/or wherein the gene FRDS1 is overexpressed, and/or one of the genes or both genes PYC1 and/or PYC2 are overexpressed.

The truncated variant of the gene MDH2 preferably encodes for an MDH2 protein that is shortened by the first 12 N-terminal amino acids and optionally by the C-terminal proline.

The microorganism may be a yeast, in particular selected from the group comprising "*Saccharomyces cerevisiae, Saccharomyces, Saccharomycecopsis, Saccharomycodes, Schizosaccharomyces, Wickerhamia, Debayomyces, Hansenula, Hanseniaspora, Pichia, Kloeckera, Candida, Zygosaccharomyces, Ogataea, Kuraishia, Komagataella, Yarrowia, Metschnikowia, Williopsis, Nakazawaea, Kluyveromyces, Cryptococcus, Torulaspora, Bullera, Rhodotorula, Willopsis, Kloeckera* and *Sporobolomyces*", and the gene FUM1 may be selected from an organism from the group comprising "*Escherichia coli, Anaerobiospirillum, Actinobacillus, Mannheimia, Corynebacterium*". At least one of the genes from the group comprising "FRDS1, PYC1 and PYC2" may be under the control of a second foreign constitutively active promotor, for instance of the ADH1-promotor.

Preferably, two natural genes MDH2 and FUM1 are replaced or supplemented and/or the two genes FRDS1 and PYC1 are overexpressed.

Such a microorganism can be used for the production of succinic acid with considerably increased yield. This is achieved by that a) the microorganism optionally is cultivated and multiplied in a growth culture medium under aerobic conditions, b) then the microorganism is cultivated under optionally anaerobic conditions, and c) after step b) or during step b), the succinic acid is separated from the culture supernatant and optionally is purified. With regard to the conditions in steps a) to c), the above explanations apply in an analogous manner.

A microorganism according to the invention can be produced by that in the wild-type microorganism or in an initial organism genetically modified or mutated with respect to the wild-type, one of the wild-type genes MDH2 or FUM1, or both of these genes, are deleted or inactivated or supplemented by that the respective variant of the MDH2 gene and/or the foreign FUM1 gene is introduced into the microorganism, and the microorganism is transformed therewith, and/or by that at least one of the genes FRDS1, PYC1 and PYC2, preferably at least both genes FRDS1 and PYC1, are introduced into the microorganism under the control of the second promotor, and the microorganism is transformed therewith.

Another advantage of the respiratory mode for the production of dicarboxylic acids is the increased expression of the enzymes pyruvate carboxylase (Pyc1p and Pyc2p), which catalyzes the reaction of pyruvate to oxalacetate, wherein carbon in the form of $CO_2$ is fixed (see FIG. 3d)). The enzymatic reaction of the pyruvate carboxylase is the first step of the reductive part of the citrate cycle (FIG. 3f.)), and of the gluconeogenesis. The gluconeogenesis, i.e. the build-up of the storage substance glycogen, takes mainly place under respiration conditions (Haurie, Perrot et al. 2001). The $CO_2$ fixation in this enzymatic step permits a process with evened-out or even positive $CO_2$ balance, which has a large environmental relevance with respect to the process.

Furthermore, in an improvement described in the following of all above alternatives of the invention, the generation of side products in the form of glycerol and ethanol (see FIG. 3c.)) and thus yield losses are reduced by the propagation of the respiration, since glycerol and ethanol represent the fermentation end products of the yeast.

The modifications of the expression profile in the course of the "diauxic shift" relates to almost one quarter of the about 6,000 genes in *Saccharomyces cerevisiae* (Young et al. 2003).

These profound modifications are induced by a few kinases and transcription factors of the catabolite repression cascade, which each develop a regulatory effect in the promotor region of a plurality of target genes. This shows that beside the genes of the respiratory central metabolism, an enormous number of further genes are repressed by glucose. For an efficient production of organic acids in yeast, it is therefore not sufficient to transcriptionally deregulate exclusively the genes of the central metabolism by overexpression. It is necessary to deprive a plurality of further glucose-repressed genes of the respiratory system of this repression. This relates to genes that encode for mitochondrial transportation systems, exchange of redox equivalents, proteins of the respiratory chain and the mitochondrial biogenesis. In a yeast strain that has no or a reduced glucose repression, the complete respiratory system is more efficient on primary and other carbon sources. Since dicarboxylic acids, such as succinic acid, fumaric acid, malic acid and oxalacetic acid are intermediates of the respiratory metabolism, such a strain is very suitable for the production of these acids. Since for reasons of the strain stability and the efficiency, only a limited number of genes can individually transcriptionally be deregulated, the suspension of the glucose-induced repression of a plurality of genes can only be achieved by influencing suitable transcription factors that are responsible for this repression, on a superior level.

In the yeast *Saccharomyces cerevisiae*, several kinases and transcription factors of the catabolite repression cascade are known and investigated, which act repressively in the promotor region of their target genes of the respiratory system. Furthermore, transcription factors are known and investigated, which lead in the course of the "diauxic shift" to an increased expression of their target genes, i.e. act in an inductive or activating manner. For the suspension or reduction of the glucose repression on a superior level, and thus for the activation of many genes of the respiratory system, suitable kinases and transcription factors must be repressed or activated. In this way, the efficiency of the production of organic acids of the respiratory system can be increased.

To sum up, a yeast strain with reduced or suspended glucose repression has by activation or repression of suitable kinases and transcription factors for the production of organic dicarboxylic acids of the respiratory central metabolism on primary carbon sources in comparison to a wild-type strain the following advantages:
- the carbon flux through the citrate and glyoxylate cycle is increased
- the strain has a higher and faster growth
- less generation of side products in the form of ethanol and glycerol
- the glyoxylate cycle is propagated
- the enzymes that are responsible for the $CO_2$ fixation in the central metabolism are expressed to an increased degree
- all genes of the respiratory system, e.g. of the mitochondrial transportation systems, the respiratory chain, the mitochondrial biogenesis and for the exchange of redox equivalents are active
- enzymes of the citrate and glyoxylate cycle are deprived of the glucose-induced negative regulation on protein level These advantages lead to a more efficient production with regard to production time and yields. Besides, the ecological efficiency is increased by that less $CO_2$ is generated and more $CO_2$ is fixed.

The yeast cell does not only exhibit the catabolite repression on glucose, but also on other fermentable $C_6$ and $C_5$ sugars, as for instance galactose or ribose, and to a lower degree also on not fermentable carbon sources, such as for instance glycerol (Gancedo 1998). Therefore, a more efficient production can be expected in a glucose-derepressed strain on all fermentable and on many not fermentable carbon sources.

In this context, on the one hand transcription factors are to be named.

The Snf1p/Snf4p complex belongs to the protein serine/threonine kinases and plays a central role for the suspension of the glucose repression in the course of the "diauxic shift". The Snf1/Snf4 complex is placed very far on top in the hierarchy of the cascade, which is responsible for the glucose repression or derepression. In the course of the "diauxic shift", the Snf1p/Snf4p complex is phosphorylated the Snf1 kinases Sak1p, Tos1p and Elm1p and thus activated (Rubenstein et al. 2006). The activated complex is localized in the nucleus, where it influences two transcription factors positioned further down in the hierarchy level. These are the proteins Mig1p and Cat8p (Treitel et al. 1998).

The zinc finger protein Mig1p is a transcriptional repressor, which recruits the proteins Tup1p and Cyc8p, in order to bind then as a complex to the corresponding consensus sequence of the promotor of a plurality of glucose-repressed genes, thereby the transcription of the subsequent gene being prevented (Treitel and Carlson 1995).

Cat8p is a transcriptional activator and induces the expression of at least 34 genes, when there is no glucose anymore in the medium. These are mainly the genes of the glyoxylate cycle, which is required for an efficient production of organic acids in yeast. Furthermore, some genes that are responsible for the intracellular transport of intermediates of the glyoxylate and citrate cycle are subject to the regulation by Cat8p (Haurie, Perrot et al. 2001).

The active Snf1p/Snf4p complex phosphorylates the Mig1 protein, whereby this is inactivated and translocalized from the cell nucleus (De Vit et al. 1997) and phosphorylates Cat8p and Sip1p, the functional homolog, which leads to an activation of these two proteins.

Thus, an active Snf1p/Snf4p complex localized in the cell nucleus substantially contributes to the suspension of the glucose repression, since it immediately influences further transcription factors of the repression cascade. This complex is composed of the proteins Snf1p and Snf4p, and respectively one of the proteins Gal83p, Sip1p and Sip2p (Jiang and Carlson 1997). The latter proteins have an influence on the localization of the total complex within the cell and represent the link of the complex. Snf4p is the regulatory and Snf1p is the catalytic subunit. Snf1p is activated by that one of the 3 redundant kinases Sak1p, Tos1p or Elm1p phosphorylates the amino acid threonine at position 210. Against this phosphorylation acts the Glc7p/Reg1p Type1 protein phosphatase (Santangelo 2006). Reg1p is the regulatory subunit of this protein phosphatase and conducts this complex by binding to Glc7p to a series of substrates, which are involved in different processes including the glucose repression, the cell growth, and the glycogen generation (Cui et al. 2004). Reg1p interacts with the kinase domain of the Snf1 protein and conducts Glc7p to the activation loop of Snf1p, which results in the dephosphorylation and inactivation of Snf1p, and thus in the glucose repression of many genes.

Frederick et al. (1996) could identify a homolog to Reg1p-Reg2p. A Δreg1 or Δreg2 mutant shows a distinctly slower growth on fermentable and not fermentable carbon sources. A Δreg1Δreg2 double mutant has even more severe deficiencies (Frederick and Tatchell 1996). The overexpression of REG2 in a Δreg1Δreg2 mutant alleviates these deficiencies with respect to the growth, the strongly reduced glucose repression is however unaffected. This shows that mainly Reg1p plays a role for maintaining the glucose repression.

In order to keep Snf1p/Snf4p in an active condition even in the presence of glucose, 2 mechanisms can be envisaged. First, the protein Sak1p, which is responsible as the main kinase for the phosphorylation and thus the activation of the Snf1p/Snf4p complex, is to be overexpressed by transcriptional deregulation of the gene SAK1.

Furthermore, the dephosphorylation by the Glc7p/Reg1p protein phosphatase is to be prevented. The repression or deletion of GLC7 leads to a nonviable cell, thus this being only possible by repression or deletion of the gene REG1.

By both measures, the regulatory duel between Sak1p and Glc7p/Reg1p can be shifted in the direction of an active Snf1p/Snf4p complex, which substantially contributes to the suspension of the glucose repression.

The Hap2/3/4/5 protein complex regulates a great number of glucose-repressed genes. These are mainly genes of the respiratory chain, and of the citrate cycle. As an activator, it induces the transcription of these genes during the "diauxic shift" and strongly contributes to the shift of the respiro-fermentative balance in the direction of respiration. The genes HAP2, HAP3 and HAP5 are constitutively expressed (Mc-Nabb and Pinto 2005). HAP4 is naturally expressed only by growth on not fermentable carbon sources. During the cultivation of an HAP4 overexpression mutant it was observed that this mutation, in comparison to the wild-type, leads to an increased growth rate, biomass and acetate production, and to a reduced ethanol and glycerol production (Blom et al. 2000). The Hap2/3/4/5 protein complex propagates the respiratory system by that the carbon flux is increased by the citrate cycle and the respiratory capacity, and the mitochondrial biogenesis is promoted.

By the overexpression of Hap4p thus the efficiency of the production of organic carboxylic acids, in particular dicarboxylic acids and hydroxy fatty acids of the respiratory central metabolism of the yeast, such as for instance succinic acid, fumaric acid, malic acid, oxalacetic acid is increased with regard to production time and yields.

Most genes that are subject to the glucose repression are regulated by several transcription factors. In the promotor region of these genes, very often binding domains for several transcription factors, such as for instance Mig1p, Hap2/4/5/6p, Cat8p etc., can be found.

Further, these proteins regulate each other. The transcription of Cat8p for instance is subject to the strict repression in the presence of glucose, mainly by the Mig1 protein, which also represses the transcription of the gene SNF1 (Schuller and Entian 1991). In the promotor region of the gene HAP4 a Mig1p binding sequence was also identified (Gancedo 1998). It could be shown that the influence of several transcription factors of the glucose repression cascade has an additive effect (Lascaris et al. 2004). Thus it becomes clear that only the combined influence of more than one transcription factor or complex can lead to a comprehensive reduction or elimination of the catabolite repression.

Therefore the invention also comprises an isolated genetically modified microorganism, in particular as an improvement of one of the variants described above, wherein one of the genes HAP4 or SAK1 is overexpressed, or wherein both genes HAP4 and SAK1 are overexpressed, and/or wherein the gene REG1 is repressed or deleted.

Preferably, this is a Crabtree-positive yeast, in particular selected from the group comprising "*Saccharomyces cerevisiae, Saccharomyces, Saccharomycecopsis, Saccharomycodes, Schizosaccharomyces, Wickerhamia, Debayomyces, Hansenula, Hanseniaspora, Pichia, Kloeckera, Candida, Zygosaccharomyces, Ogataea, Kuraishia, Komagataella, Yarrowia, Metschnikowia, Williopsis, Nakazawaea, Kluyveromyces, Cryptococcus, Torulaspora, Bullera, Rhodotorula, Willopsis, Kloeckera* and *Sporobolomyces*".

In particular, one of the genes HAP4 or SAK1, or both genes can be under the control of a second foreign, constitutively active promotor, in particular of the ADH1-promotor.

Such microorganisms generally are suitable for the production of organic carboxylic acids, in particular of succinic acid, fumaric acid, malic acid, oxalacetic acid, lactic acid, acetic acid, and/or formic acid, with increased yields. Which carboxylic acid is formed with particularly high yield, depends on the further genetic measures, as described above. With regard to the production of the carboxylic acids, the above explanations apply in an analogous manner.

Finally, the invention relates to a method for the production of such a microorganism, wherein in the wild-type microorganism or in an initial organism genetically modified or mutated with respect to the wild-type, the wild-type gene REG1 is deleted or inactivated, and/or wherein at least one of the genes HAP4 or SAK1, preferably both genes are introduced under the control of the second promotor into the microorganism, and the microorganism is transformed therewith. Optionally, the measures may in addition be reasonable that are described above in context with further variants of microorganisms according to the invention.

The genes used for the purpose of the alternatives and/or improvements described above or the nucleic acid sequences thereof are described in the NCBI database with the following Accession Nos.:
HAP4: NP_012813
REG1: NP_010311
SAK1: NP_011055
MDH2: NP_014515
FRDS1: NP_010867
fumB: NC_004431
aceA: U00096 AE000111-AE000510

The above documents have the following bibliographic data:

Blom, J., M. J. De Mattos and L. A. Grivell (2000). "Redirection of the respiro-fermentative flux distribution in *Saccharomyces cerevisiae* by overexpression of the transcription factor Hap4p." Appl Environ Microbiol 66(5):1970-3.

Cui, D. Y., C. R. Brown and H. L. Chiang (2004). "The type 1 phosphatase Reg1p-Glc7p is required for the glucose-induced degradation of fructose-1,6-bisphosphatase in the vacuole." J Biol Chem 279(11):9713-24.

De Vit, M. J., J. A. Waddle and M. Johnston (1997). "Regulated nuclear translocation of the Mig1 glucose repressor." Mol Biol Cell 8(8): 1603-18.

Frederick, D. L. and K. Tatchell (1996). "The REG2 gene of *Saccharomyces cerevisiae* encodes a type 1 protein phosphatase-binding protein that functions with Reg1p and the Snf1 protein kinase to regulate growth." Mol Cell Biol 16(6):2922-31.

Gancedo, J. M. (1998). "Yeast carbon catabolite repression." Microbiol Mol Biol Rev 62(2): 334-61.

Haurie, V., M. Perrot, T. Mini, P. Jeno, F. Sagliocco and H. Boucherie (2001). "The transcriptional activator Cat8p provides a major contribution to the reprogramming of carbon metabolism during the diauxic shift in *Saccharomyces cerevisiae*." J Biol Chem 276(1):76-85.

Hung, G. C., C. R. Brown, A. B. Wolfe, J. Liu and H. L. Chiang (2004). "Degradation of the gluconeogenic enzymes fructose-1,6-bisphosphatase and malate dehydrogenase is mediated by distinct proteolytic pathways and signaling events." J Biol Chem 279(47):49138-50.

Jiang, R. and M. Carlson (1997). "The Snf1 protein kinase and its activating subunit, Snf4, interact with distinct domains of the Sip1/Sip2/Gal83 component in the kinase complex." Mol Cell Biol 17(4):2099-106.

Lascaris, R., J. Piwowarski, H. van the Spek, J. Teixeira de Mattos, L. Grivell and J. Blom (2004). "Overexpression of HAP4 in glucose-derepressed yeast cells reveals respiratory control of glucose-regulated genes." Microbiology 150(Pt 4):929-34.

Lopez-Boado, Y. S., P. Herrero, T. Fernandez, R. Fernandez and F. Moreno (1988). "Glucose-stimulated phosphorylation of yeast isocitrate lyase in vivo." J Gen Microbiol 134(9):2499-505.

McNabb, D. S. and I. Pinto (2005). "Assembly of the Hap2p/Hap3p/Hap4p/Hap5p-DNA complex in *Saccharomyces cerevisiae*." Eukaryot Cell 4 (11): 1829-39.

Ordiz, I., P. Herrero, R. Rodicio and F. Moreno (1996) "Glucose-induced inactivation of isocitrate lyase in *Saccharomyces cerevisiae* is mediated by the cAMP-dependent protein kinase catalytic subunits Tpk1 and Tpk2." FEBS Lett 385(1-2):43-6.

Rubenstein, E. M., R. R. McCartney and M. C. Schmidt (2006). "Regulatory domains of Snf1-activating kinases determine pathway specificity." Eukaryot Cell 5(4):620-7.

Santangelo, G. M. (2006). "Glucose signaling in *Saccharomyces cerevisiae*." Microbiol Mol Biol Rev 70(1):253-82.

Sass, E., S. Karniely and O. Pines (2003). "Folding of fumarase during mitochondrial import determines its dual targeting in yeast." J Biol Chem 278(46):45109-16.

Schuller, H. J. and K. O. Entian (1991). "Extragenic suppressors of yeast glucose derepression mutants leading to constitutive synthesis of several glucose-repressible enzymes." J Bacteriol 173(6):2045-52.

Treitel, M. A. and M. Carlson (1995). "Repression by SSN6 TUP1 is directed by MIG1, a repressor/activator protein." Proc Natl Acad Sci USA 92(8):3132-6.

Treitel, M. A., S. Kuchin and M. Carlson (1998). "Snf1 protein kinase regulates phosphorylation of the Mig1 repressor in *Saccharomyces cerevisiae*." Mol Cell Biol 18(11}: 6273-80.

Young, E. T., K. M. Dombek, C. Tachibana and T. Ideker (2003). "Multiple pathways are co-regulated by the protein kinase Snf1 and the transcription factors Adr1 and Cat8." J Biol Chem 278(28):26146-58.

In the following, the invention is explained in more detail by reference to embodiments.

EXAMPLE 1

Production of a Microorganism with Tetracycline-Regulated Promotor System

In order to achieve an interruption of the citrate cycle after termination of the biomass growth, according to the invention, three genes of this metabolic pathway are controlled by promotors that can be regulated. These are the gene IDH1, which encodes the first subunit of the NAD-dependent isocitrate dehydrogenase, and the gene SDH2, which encodes for a subunit of the succinate dehydrogenase, and the gene DIC1, which encodes for the mitochondrial dicarboxylate transporter. An elimination of these enzyme activities has the consequence that isocitrate, the substrate of the glyoxylate cycle, is not transformed anymore by the citrate cycle into 2-oxoglutarate, and succinic acid is not metabolized into fumarate, and the succinate of the glyoxylate cycle is not transported anymore into the mitochondrion and is thus not fed anymore to the citrate cycle localized in the mitochondrion. Thus, the citrate cycle is interrupted. The promotors to be used have the important property to be active during the growth phase, in order to permit the operation of the citrate cycle and to be repressed as strongly as possible in the production phase by addition of a repressor. This regulation is made possible, beside the repressible tetO promotor, by the second component of the tetracycline-regulated promotor system. This is the transcriptional transactivator (tTA), which represents a fusion protein of an operator binding domain and an activation domain. tTA binds to the tetO promotor, which has as a consequence the transcription of the subsequent gene. Antibiotics from the group of the tetracyclines induce a conformation change of the tTA, which leads to its detachment from the tetO promotor and thereby the transcription of the subsequent gene is prevented. In order to secure the operation of the tetO promotor, thus also the gene for the tTA is to be integrated in the genome of the corresponding microorganism. For this, for instance the LEU2 locus is available.

Isocitrate dehydrogenase, succinate dehydrogenase and dicarboxylate transporter are expressed during the growth phase under the control of the tetO promotor repressible by tetracycline. During the production phase, the enzyme activities are eliminated in a controlled manner. *Saccharomyces cerevisiae* is so modified that the natural promotors of the three target genes are exchanged by the repressible promotor e.g. by specific integration in the yeast genome.

The construction of the thus obtained yeast strain *S. cerevisiae* GRFura3 tTA tetOprom-SDH2 and tetOprom-IDH1 and tetOprom-DIC1 results from the following Table 1.

TABLE 1

| Strain | Description |
|---|---|
| GRFura3 | leu2, ura3, his3 |
| GRFura3tTA | tTA::Leu2, leu2, ura3, his3 |
| GRFura3tTArepr.SDH2 | tetOprom::sdh2prom, leu2, his3, ura3 tTA::Leu2 |
| Fura3 | tTA::Leu2, tetOprom::sdh2prom, tetOprom::idh1prom |
| repr.SDH2 repr.IDH1 repr.DIC1 | tetOprom::dic1prom, leu2, his3, ura3 |
| ]=GRFura3tTArepr.SDH2 repr.IDH1repr.DIC1 | |

EXAMPLE 2

Microorganism with Constitutively Active Succinic Acid Synthesis

Since the glyoxylate cycle and other reactions on the way to the succinic acid biosynthesis are naturally transcriptionally strongly repressed in the yeast cell in the presence of glucose, with the consequence that this biosynthesis pathway is not active, all or a selection of enzymes of this metabolic pathway and the pyruvate carboxylase, the enzyme that is responsible for the anaplerotic reaction ($CO_2$ fixation), are transcriptionally preferably deregulated during the production phase for the biosynthesis of succinic acid from glucose. For the deregulated expression of the genes in the yeast *Saccharomyces cerevisiae*, the constitutive ADH1 promotor is used, which leads by modification of the natural sequence for a very long time to a constitutive expression independent from glucose and ethanol (see Lang C., Looman A. C., Appl Microbiol Biotechnol. 44(1-2):147-156 (1995). Transcriptionally deregulated are the genes PYC1, ACS1, CIT1, ACO1, ICL1, MLS1, MDH3 and CIT2. For this purpose, an expression system is used, which permits the simultaneous transcriptionally deregulated expression of PYC1, ACS1, CIT1, ACO1, ICL1, MLS1, MDH3 and CIT2. The individual genes (PYC1, ACS1, CIT1, ACO1, ICL1, MLS1, MDH3 and CIT2) were amplified from chromosomal yeast DNA of the strain *S. cerevisiae* S288c by means of PCR and provided with restriction linkers and then integrated individually in the yeast chromosome under the control of the constitutive ADH1 promotor.

The construction of the thus obtained yeast strain *S. cerevisiae* results from the Table 2.

TABLE 2

| Strain | Description |
|---|---|
| GRFura3tTa repr.SDH2 repr.IDH1 repr.DIC1 | tTA::Leu2, tetOprom::sdh2prom, tetO₇prom::idh1prom, tetOprom::die1prom his3, ura3, leu2 |
| GRFura3tTA repr.SDH2 repr.IDH1 repr.DIC1 der.PYC1 | tTA::Leu2, tetOprom::sdh2prom, tetO₇prom::idh1prom, tetO₇prom::die1prom, der.pYC1::pyc1, his3, ura3, leu2 |
| GRFura3tTA repr.SDH2 repr.IDH1 repr.DIC1 der.PYC1 der.ACS1 | tTA::Leu2, tetOprom::sdh2prom, tetOprom::idh1prom, tetOprom::dic1prom, der.PYC1::pyc1, der.ACS1::acs1, his3, ura3, leu2 |
| GRFura3tTA repr.SDH2 repr.IDH1 repr.DIC1 der.PYC1 der.ACS1 der.CIT1 | tTA::Leu2, tetOprom::sdh2prom, tetOprom::idh1prom, tetOprom::dic1prom, der.PYC1::pyc1, der.ACS1::acs1, der.CIT1::cit1, his3, ura3, leu2 |
| GRFura3tTA repr.SDH2 repr.IDH1 repr.DIC1 der.PYC1 der.ACS1 der.CIT1 der.ACO1 | tTA::Leu2, tetOprom::sdh2prom, tetOprom::idh1prom, tetOprom::dic1prom, der.PYC1::pyc1, der.ACS1::acs1, der.CIT1::cit1, der.ACO1::aco1, his3, ura3, leu2 |
| GRFura3tTA repr.SDH2 repr.IDH1 | tTA::Leu2, tetOprom::sdh2prom, tetOprom::idh1prom, tetOprom::dic1prom, der.PYC1::pyc1, der.ACS1::acs1, der.CIT1::cit1, der.ACO1::aco1, der.ICL1::icl1, his3, ura3, leu2 |
| repr.DIC1 der.PYC1 der.ACS1 der.CIT1 der.ACO1 der.ICL1 | |
| GRFura3tTA repr.SDH2 repr.IDH1 repr.DIC1 der.PYC1 der.ACS1 der.CIT1 der.ACO1 der.ICL1 der.MLS1 | tTA::Leu2, tetOprom::sdh2prom, tetOprom::idh1prom, tetOprom::dic1prom, der.PYC1::pyc1, der.ACS1::acs1, der.CIT1::cit1, der.ACO1::aco1, der.ICL1::icl1, der.MLS1::mls1, his3, ura3, leu2 |
| GRFura3tTA repr.SDH2 repr.IDH1 repr.DIC1 der.PYC1 der.ACS1 der.CIT1 der.ACO1 der.ICL1 der.MLS1 der.MDH3 | tTA::Leu2, tetOprom::sdh2prom, tetOprom::idh1prom, tetOprom::dic1prom, der.PYC1::pyc1, der.ACS1::acs1, der.CIT1::cit1, der.ACO1::aco1, der.ICL1::icl1, der.MLS1::mls1, der.MDH3::mdh3, his3, ura3, leu2 |
| GRFura3tTA repr.SDH2 repr.IDH1 | tTA::Leu2, tetOprom::sdh2prom, tetOprom::idh1prom, tetOprom::dic1prom, der.PYC1::pyc1, der.ACS1::acs1, der.CIT1::cit1, der.ACO1::aco1, der.ICL1::icl1, |

TABLE 2-continued

| Strain | Description |
|---|---|
| repr.DIC1 der.PYC1 der.ACS1 der.CIT1 der.ACO1 der.ICL1 der.MLS1 der.MDH3 der.CIT2 | der.MLS1::mls1, der.MDH3::mdh3, der.CIT2::cit2, his3, ura3, leu2 |

EXAMPLE 3

Expression of the Transcriptional Transactivator Under the Control of the CMV Promotor at the Locus LEU2 in *S. Cerevisiae* GRFura3

The encoding nucleic acid sequence for the tTA-expression cassette was amplified by PCR standard methods, so that the resulting fragment consists of the following components: loxP-kanMX-loxP-CMVprom.-tTA (YEAST 20:1255-1262, 2003). As primers, oligonucleotide sequences are chosen that at the 5' and 3' overhangs respectively contain the 5' or the 3' sequence of the LEU2 gene and in the annealing section the sequences 5' of the loxP region and 3' of the tTA gene. Thus it is secured that on the one hand the complete fragment including KanR and tTA is amplified and on the other hand this fragment can then be transformed into yeast and by homologous recombination this complete fragment is integrated in the LEU2 gene locus of the yeast.

As a selection marker serves the resistance against G418. The resulting strain *S. cerevisiae* GRFura3 tTA contains a copy of the gene tTA under the control of the CMV promoter. In order to then remove again the resistance against G418, the generated yeast strain is transformed with the cre recombinase vector pSH47 (Guldener U, Heck S, Fielder T, Beinhauer J, Hegemann J H. (1996) A new efficient gene disruption cassette for repeated use in budding yeast. Nucleic Acids Res. July 1; 24(13):2519-24). By this vector, the cre recombinase is expressed in the yeast, with the consequence that the sequence region within the two loxP sequences will recombine out. The consequence is that only one of the two loxP sequences and the CMVprom.-tTA cassette remain contained in the original LEU2 gene locus. The consequence is that the yeast strain loses again the G418 resistance and is thus suitable to integrate or remove further genes by means of this cre-lox system in the yeast strain. The vector pSH47 can then be removed again by a counter-selection on YNB agar plates supplemented with uracil (20 mg/L) and FOA (5-fluoroorotic acid) (1 g/L). For this purpose, the cells that carry this plasmid must first be cultivated under not selective conditions and then be drawn on FOA-containing selective plates. Under these conditions, only those cells can grow that are not capable themselves to synthesize uracil. These are in this case cells that do not contain plasmid (pSH47) anymore.

EXAMPLE 4

Expression of SDH2 Under the Control of the Tetracycline-Regulated TetO₇ Promotor in *S. Cerevisiae* GRFura3

The encoding nucleic acid sequence for the tetO₇ promotor cassette was amplified by PCR and standard methods, so that the resulting fragment consists of the following components:

loxP-kanMX-loxP-ADH1term.-tetO$_7$operator-CYC1prom. (YEAST 13:837-848 (1997); Nucleic Acid Research 24(13): 1519-2524 (1996)). As primers, oligonucleotide sequences were chosen that at the 5' and 3' overhangs respectively contain the 5' or the 3' sequence of the native promoter of the SDH2 gene and in the annealing section the sequences 5' of the loxP region and 3' of the CYC1prom. Thus it is secured that on the one hand the complete fragment including KanR and tetO$_7$ promotor is amplified and on the other hand this fragment can then be transformed into yeast and by homologous recombination this complete fragment is integrated in the SDH2 gene locus of the yeast, before the encoding region of the gene SDH2.

As a selection marker serves the resistance against G418. The resulting strain *S. cerevisiae* GRFura3 repr.SDH2 contains a copy of the gene SDH2 under the control of the tetracycline regulated tetO$_7$ promotor and of the native SDH2 terminator. In order to then remove again the resistance against G418, the generated yeast strain is transformed with the cre recombinase vector pSH47 (Guldener U, Heck S, Fielder T, Beinhauer J, Hegemann J H. (1996): A new efficient gene disruption cassette for repeated use in budding yeast. Nucleic Acids Res. July 1; 24(13):2519-24). By this vector, the cre recombinase is expressed in the yeast, with the consequence that the sequence region within the two loxP sequences will recombine out. The consequence is that only one of the two loxP sequences and the tetO$_7$ promotor cassette remains contained before the encoding sequence of the gene SDH2. The consequence is that the yeast strain loses again the G418 resistance and is thus suitable to integrate or remove further genes by means of this cre-lox system in the yeast strain. The vector pSH47 can then be removed again by a counter-selection on YNB agar plates supplemented with uracil (20 mg/L) and FOA (5-fluoroorotic acid) (1 g/L). For this purpose, the cells that carry this plasmid must first be cultivated under not selective conditions and then be drawn on FOA-containing selective plates. Under these conditions, only those cells can grow that are not capable themselves to synthesize uracil. These are in this case cells that do not contain plasmid (pSH47) anymore.

EXAMPLE 5

Expression of IDH1 Under the Control of the Tetracycline-Regulated TetO$_7$ Promotor in *S. Cerevisiae* GRFura3

The encoding nucleic acid sequence for the tetO$_7$ promotor cassette was amplified by PCR and standard methods, so that the resulting fragment consists of the following components: loxP-kanMX-loxP-ADH1term.-tetO$_7$operator-CYC1prom. (YEAST 13:837-848 (1997); Nucleic Acid Research 24(13): 1519-2524 (1996)). As primers, oligonucleotide sequences were chosen that at the 5' and 3' overhangs respectively contain the 5' or the 3' sequence of the native promoter of the IDH1 gene and in the annealing section the sequences 5' of the loxP region and 3' of the CYC1prom. Thus it is secured that on the one hand the complete fragment including KanR and tetO$_7$ promotor is amplified and on the other hand this fragment can then be transformed into yeast and by homologous recombination this complete fragment is integrated in the IDH1 gene locus of the yeast, before the encoding region of the gene IDH1.

As a selection marker serves the resistance against G418. The resulting strain *S. cerevisiae* GRFura3 repr.IDH1 contains a copy of the gene IDH1 under the control of the tetracycline regulated tetO$_7$ promotor and of the native IDH1 terminator. In order to then remove again the resistance against G418, the generated yeast strain is transformed with the cre recombinase vector pSH47 (Guldener U, Heck S, Fielder T, Beinhauer J, Hegemann J H. (1996): A new efficient gene disruption cassette for repeated use in budding yeast. Nucleic Acids Res. July 1; 24(13):2519-24). By this vector, the cre recombinase is expressed in the yeast, with the consequence that the sequence region within the two loxP sequences will recombine out. The consequence is that only one of the two loxP sequences and the tetO$_7$ promotor cassette remain contained before the encoding sequence of the gene IDH1. The consequence is that the yeast strain loses again the G418 resistance and is thus suitable to integrate or remove further genes by means of this cre-lox system in the yeast strain. The vector pSH47 can then be removed again by a counter-selection on YNB agar plates supplemented with uracil (20 mg/L) and FOA (5-fluoroorotic acid) (1 g/L). For this purpose, the cells that carry this plasmid, must first be cultivated under not selective conditions and then be drawn on FOA-containing selective plates. Under these conditions, only those cells can grow that are not capable themselves to synthesize uracil. These are in this case cells that do not contain plasmid (pSH47) anymore.

EXAMPLE 6

Expression of DIC1 Under the Control of the Tetracycline-Regulated TetO$_7$ Promotor in *S. Cerevisiae* GRFura3

The encoding nucleic acid sequence for the tetO$_7$ promotor cassette was amplified by PCR and standard methods, so that the resulting fragment consists of the following components: loxP-kanMX-loxP-ADH1term.-tetO$_7$operator-CYC1prom. (YEAST 13:837-848 (1997); Nucleic Acid Research 24(13): 1519-2524 (1996)). As primers, oligonucleotide sequences were chosen that at the 5' and 3' overhangs respectively contain the 5' or the 3' sequence of the native promoter of the DIC1 gene and in the annealing section the sequences 5' of the loxP region and 3' of the CYC1prom. Thus it is secured that on the one hand the complete fragment including KanR and tetO$_7$ promotor is amplified and on the other hand this fragment can then be transformed into yeast and by homologous recombination this complete fragment is integrated in the DIC1 gene locus of the yeast, before the encoding region of the gene DIC1.

As a selection marker serves the resistance against G418. The resulting strain *S. cerevisiae* GRFura3 repr.DIC1 contains a copy of the gene DIC1 under the control of the tetracycline regulated tetO$_7$ promotor and of the native DIC1 terminator. In order to then remove again the resistance against G418, the generated yeast strain is transformed with the cre recombinase vector pSH47 (Guldener U, Heck S, Fielder T, Beinhauer J, Hegemann J H. (1996): A new efficient gene disruption cassette for repeated use in budding yeast. Nucleic Acids Res. July 1; 24(13):2519-24). By this vector, the cre recombinase is expressed in the yeast, with the consequence that the sequence region within the two loxP sequences will recombine out. The consequence is that only one of the two loxP sequences and the tetO$_7$ promotor cassette remains contained before the encoding sequence of the gene IDH1. The consequence is that the yeast strain loses again the G418 resistance and is thus suitable to integrate or remove further genes by means of this cre-lox system in the yeast strain. The vector pSH47 can then be removed again by a counter-selection on YNB agar plates supplemented with uracil (20 mg/L) and FOA (5-fluoroorotic acid) (1 g/L). For this purpose, the cells that carry this plasmid must first be cultivated under not selective conditions and then be drawn on FOA-containing selective plates. Under these conditions, only those cells can grow that are not capable themselves to synthesize uracil. These are in this case cells that do not contain plasmid (pSH47) anymore.

EXAMPLE 7

Expression of PYC1, ACS1, CIT1, ACO1, CIT2, ICL1, MLS1 and MDH3 Under the Control of the Constitutive ADH1 Promotor in S. Cerevisiae GRFura3tTArepr.SDH2repr.IDH1repr.DIC1

The following description applies to the sequential execution of the integration of transcriptionally deregulated genes for the mentioned genes, following the same scheme.

The encoding nucleic acid sequence for the expression cassette of ADH1prom-PYC1 (ACS1, CIT1, ACO1, CIT2, ICL1, MLS1, MDH3)-TRP1term was amplified by PCR and standard methods from the vector pFlat-PYC1 (ACS1, CIT1, ACO1, CIT2, ICL1, MLS1, MDH3). The obtained DNA fragment was blunt-end cloned after a Klenow treatment into the vector pUG6 in the EcoRV interface and resulted in the vector pUG6-PYC1 (ACS1, CIT1, ACO1, CIT2, ICL1, MLS1, MDH3). After plasmid isolation, an extended fragment of the vector pUG6-PYC1 (ACS1, CIT1, ACO1, CIT2, ICL1, MLS1, MDH3) was amplified by means of PCR, so that the resulting fragment consists of the following components: loxP-kanMX-loxP-ADH1prom-PYC1 (ACS1, CIT1, ACO1, CIT2, ICL1, MLS1, MDH3) tryptophan terminator. As primers, oligonucleotide sequences were chosen that at the 5' and 3' overhangs respectively contain the 5' or the 3' sequence of the PYC1 (ACS1, CIT1, ACO1, CIT2, ICL1, MLS1, MDH3) gene and in the annealing section the sequences 5' of the loxP region and 3' of the tryptophan terminator. Thus it is secured that on the one hand the complete fragment including KanR and PYC1 (ACS1, CIT1, ACO1, CIT2, ICL1, MLS1, MDH3) is amplified and on the other hand this fragment can then be transformed into yeast and by homologous recombination this complete fragment is integrated in the PYC1 (ACS1, CIT1, ACO1, CIT2, ICL1, MLS1, MDH3) gene locus of the yeast.

As a selection marker serves the respective resistance against G418. The resulting strain S. cerevisiae GRFura3tTA repr.SDH2 repr.IDH1 repr.DIC1 dereg.PYC1 ACS1 CIT1 ACO1 ICL1 MLS1 MDH3 CIT2 contains a copy of the gene SDH2, IDH1 and DIC1 under the control of the tetO$_7$ promotor and of the native terminators and one copy each of the genes PYC1, CIT1, ACS1, ACO1, ICL1, MLS1, MDH3 and CIT2 under the control of the constitutive ADH1 promotor and the TRP1 terminator. In order to then remove again the resistance against G418, the respectively generated yeast strain is transformed with the cre recombinase vector pSH47 (Guldener U, Heck S, Fielder T, Beinhauer J, Hegemann J H. (1996): A new efficient gene disruption cassette for repeated use in budding yeast. Nucleic Acids Res. July 1; 24(13):2519-24). By this vector, the cre recombinase is expressed in the yeast, with the consequence that the sequence region within the two loxP sequences will recombine out. The consequence is that only one of the two loxP sequences and the respective expression cassette remains contained in the original respective gene locus. The consequence is that the yeast strain loses again the G418 resistance and is thus suitable to integrate or remove further genes by means of this cre-lox system in the yeast strain. The vector pSH47 can then be removed again by a counter-selection on YNB agar plates supplemented with uracil (20 mg/L) and FOA (5-fluoroorotic acid) (1 g/L). For this purpose, the cells that carry this plasmid must first be cultivated under not selective conditions and then be drawn on FOA-containing selective plates. Under these conditions, only those cells can grow that are not capable themselves to synthesize uracil. These are in this case cells that do not contain plasmid (pSH47) anymore.

EXAMPLE 8

Determination of the Succinic Acid Content in Yeast Cultures of the Yeast Strain According to the Invention as Described Above in Comparison to the Corresponding Control Strain S. Cerevisiae GRFura3

The yeast strain according to the invention as described above and S. cerevisiae GRFura3 are each cultivated for 48 hours in WMVIII medium (Lang and Lomann, 1995) at 28° C. and 160 rpm in a 20 ml culture volume. Then, 500 µl of this preculture are transferred into a 50 ml main culture of the same medium and each cultivated for 2 days at 28° C. and 160 rpm in a shake flask. After obtaining the cell-free culture supernatant, the content of succinic acid, acetic acid and ethanol is determined by means of HPCL analysis. There result for the yeast strain according to the invention strongly increased succinic acid concentrations, compared to the comparison strain.

EXAMPLE 9

Microorganism with Constitutively Active Reductive Citrate Cycle for the Production of Organic Acids, in Particular Succinic Acid The reductive citrate cycle, i.e. the not cyclic return part of the citrate cycle starting from pyruvate and oxalacetate, malate and fumarate to succinate (FIG. 3f.) is the prerequisite for the maximum molar yield for the production of succinic acid on glucose. Only the reductive citrate cycle in combination with the glyoxylate cycle permits during the production of succinic acid maximum yields of up to 1.71 mol succinate per mol glucose by reoxidation of NADH to NAD+ and $CO_2$ fixation.

The reaction of the transcriptional deregulation of the gene PYC1 is explained in Example 2 and Example 7. PYC1 encodes for one of the two pyruvate carboxylases, which catalyze the $CO_2$-fixing reaction of pyruvate to oxalacetate, which is the first step of the reductive citrate cycle.

The next step, i.e. the reaction of oxalacetate to malate, catalyzes the cytosolic malate dehydrogenase (Mdh2p), which is subject to an increased proteolytic degradation induced by glucose.

This proteolytic degradation is prevented by that the malate dehydrogenase (Mdh2p) is expressed as an Mdh2p protein shortened by the first 12 N-terminal amino acids. For this purpose, an MDH2 gene correspondingly shortened at the beginning of the "open reading frame" (MDH2t, t=truncated, shortened) from chromosomal yeast DNA of the strain S. cerevisiae S288c is amplified by means of PCR and provided with restriction linkers and then integrated in the yeast chromosome under the control of the constitutive ADH1 promotor. For the deregulated expression of this shortened gene in the yeast Saccharomyces cerevisiae, the constitutive ADH1 promotor is used, which leads by modification of the natural sequence over a very long time to a constitutive expression being independent from glucose and ethanol (Lang and Looman, 1995).

The next step for the succinate production over the reductive part of the citrate cycle is the reaction of malate to fumarate. This reaction is catalyzed by the enzyme fumarase (Fum1p). The reaction of malate to fumarate is thermodynamically very unfavorable, since the fumarase has a 17 times higher affinity to fumarate than to malate.

Therefore, a fumarase enzyme is expressed heterologously in the yeast that originates from an organism, which naturally operates a mixed acid fermentation, since the thermodynamics of the fumarase of such organisms with respect to the reaction of malate to fumarate is much more favorable than in *Saccharomyces cerevisiae*.

For this purpose, the gene fumB from chromosomal bacterial DNA of the strain *E. coli* JM109 is amplified by means of PCR and provided with restriction linkers and then integrated in the yeast chromosome under the control of the constitutive ADH1 promotor. For the deregulated expression of this gene in the yeast *Saccharomyces cerevisiae*, the constitutive ADH1 promotor is used, which leads by modification of the natural sequence over a very long time to a constitutive expression being independent from glucose and ethanol (Lang and Looman, 1995).

The last step for the succinate production over the reductive citrate cycle is the reaction of fumarate to succinate. This reaction is catalyzed in the cytosol by the enzyme fumarate reductase (Frds1p). An overexpression of this enzyme increases the efficiency of the reductive succinate production. For this purpose, the FRDS1 gene from chromosomal yeast DNA of the strain *S. cerevisiae* S288c is amplified by means of PCR and provided with restriction linkers and then integrated in the yeast chromosome under the control of the constitutive ADH1 promotor. For the deregulated expression of this shortened gene in the yeast *Saccharomyces cerevisiae*, the constitutive ADH1 promotor is used, which leads by modification of the natural sequence over a very long time to a constitutive expression being independent from glucose and ethanol (Lang and Looman, 1995).

The glucose-induced proteolytic degradation or inactivation by phosphorylation of the yeast-own isocitrate lyase, one of the main enzymes of the glyoxylate cycle, is avoided by that a heterologous isocitrate lyase is expressed in the yeast *Saccharomyces cerevisiae*. This enzyme originates from a microorganism that naturally comprises a glyoxylate cycle and is "Crabtree"-negative, since an isocitrate lyase from such an organism is not subject to the glucose-induced negative regulation, or to the proteolytic degradation on protein level. An active glyoxylate cycle is essential for an efficient production of organic acids with high yields on primary carbon sources.

For this purpose, the gene aceA from bacterial DNA of the strain *E. coli* JM109 is amplified by means of PCR and provided with restriction linkers and then integrated in the yeast chromosome under the control of the constitutive ADH1 promotor. For the deregulated expression of this gene in the yeast *Saccharomyces cerevisiae*, the constitutive ADH1 promotor is used, which leads by modification of the natural sequence over a very long time to a constitutive expression being independent from glucose and ethanol (Lang and Looman, 1995).

EXAMPLE 10

Production of a Microorganism with Reduced or Inactivated Catabolite or Glucose Repression for the Production of Organic Acids of the Respiratory Central Metabolism The measures described in the following may be reasonable in addition to the measures of the examples described above, since thereby in all variants better yields are obtained.

The reduced glucose repression in the presence of glucose is obtained by specific influence of suitable transcription factors and kinases, which are responsible for the glucose repression. In this way, the efficiency of the production of organic carboxylic acids, in particular dicarboxylic acids and hydroxy fatty acids of the respiratory central metabolism of the yeast, such as for instance succinic acid, fumaric acid, malic acid, oxalacetic acid is increased with regard to production time and yields on primary carbon sources, such as e.g. glucose and other hexoses and pentoses.

This increase of the production efficiency of organic carboxylic acids on primary carbon sources results from the following properties, which a strain with reduced or suspended glucose repression comprises, in comparison to the wild-type:

the carbon flux is increased by the citrate and glyoxylate cycle
the strain has a higher and faster growth
less generation of side products in the form of ethanol and glycerol
the glyoxylate cycle is propagated
the enzymes that are responsible for the $CO_2$ fixation in the central metabolism are expressed to an increased degree
all genes of the respiratory system, e.g. of the mitochondrial transportation systems, the respiratory chain, the mitochondrial biogenesis and for the exchange of redox equivalents are active
enzymes of the citrate and glyoxylate cycle are removed from the glucose-induced negative regulation on protein level In order to achieve a specific reduction of the glucose repression in the presence of glucose or other primary carbon sources, 2 genes are transcriptionally deregulated or overexpressed, which are strongly repressed in the presence of glucose. For the deregulated expression of these genes in the yeast *Saccharomyces cerevisiae*, the constitutive ADH1 promotor is used, which leads by modification of the natural sequence over a very long time to a constitutive expression being independent from glucose and ethanol (Lang and Looman, 1995).

The genes HAP4 and SAK1 are transcriptionally deregulated. Hap4p is part of the transcriptional activator complex Hap2/3/4/5 and Sak1p is the main kinase for the phosphorylation and thus activation of the Snf1/Snf4 complex. For this purpose, an expression system was used, which permits the simultaneous transcriptionally deregulated expression of HAP4 and SAK1.

The two genes (HAP4 and SAK1) are amplified from chromosomal yeast DNA of the strain *S. cerevisiae* S288c by means of PCR and provided with restriction linkers and then individually integrated in the yeast chromosome under the control of the constitutive ADH1 promotor.

In order to obtain a specific reduction of the glucose repression in the presence of glucose or other primary carbon sources, further a gene of the glucose repression cascade is deleted or controlled by regulated promotors. This is the gene REG1, which encodes the regulatory subunit of the Glc7p/Reg1p Type 1 protein phosphatase. A not active Glc7p/Reg1p phosphatase leads to that the Snf1/Snf4 complex is phosphorylated and thus remains active, which considerably contributes to the reduction or suspension of the glucose repression.

Since an inactive gene REG1 leads to growth defects in the yeast *Saccharomyces cerevisiae*, the tetO promotor regulated by tetracycline is included before this gene. During the growth phase of the carboxylic acid production process, the gene REG1 is expressed under the control of the tetO promotor repressible by tetracycline. During the production phase, the gene expression and thus the enzyme activity of Reg1p is eliminated in a regulated manner by addition of a cultivation additive, e.g. tetracycline, to the culture medium. *Saccharomyces cerevisiae* is modified such that the natural promotor of the target gene is exchanged by the repressible promotor e.g. by targeted integration in the yeast genome, and that the yeast strain contains, as described in Example 1, the transcriptional transactivator (tTA) required for the tetO promotor system.

The practical implementation of a gene REG1 regulated under the tetO promotor can be achieved in full agreement with Examples 4 to 6, only in place of the genes there controlled by the tetO promotor, the gene REG1 has to be used.

The invention claimed is:

1. An isolated genetically modified yeast, wherein the natural gene malate dehydrogenase 2 (MDH2) is replaced or supplemented by a truncated variant of the gene malate dehydrogenase 2 (MDH2), and the natural gene fumarase 1 (FUM1) is replaced or supplemented by the gene fumarase 1 (FUM1) from an organism being different from the yeast, and wherein the gene soluble fumarase reductase 1 (FRDS1) is overexpressed, and one of the genes or both genes pyruvate carboxylase 1 (PYC1) and/or pyruvate carboxylase 2 (PYC2) are overexpressed.

2. The yeast according to claim 1, wherein the truncated variant of the gene malate dehydrogenase 2 (MDH2) encodes for an malate dehydrogenase 2 (MDH2) protein that is shortened by the first 12 N-terminal amino acids and, optionally, the C-terminal proline.

3. The yeast according to claim 1, wherein the yeast, selected from the group comprising *Saccharomyces cerevisiae, Saccharomyces, Saccharomycecopsis, Saccharomycodes, Schizosaccharomyces, Wickerhamia, Debayomyces, Hansenula, Hanseniaspora, Pichia, Kloeckera, Candida, Zygosac-charomyces, Ogataea, Kuraishia, Komagataella, Yarrowia, Metschnikowia, Williopsis, Nakazawaea, Kluyveromyces, Cryptococcus, Torulaspora, Bullera, Rhodotorula, Willopsis, Kloeckera* and a *Sporobolomyces*, and wherein the gene fumarase 1 (FUM1) is selected from an organism from the group comprising *Escherichia coli, Anaerobiospirillum succiniciproducens, Actinobacillus succinogenes, Mannheimia succiniciproducens*, and a *Corynebacterium glutamicum*.

4. The yeast according to claim 1, wherein at least one of the genes from the group comprising soluble fumarase reductase 1 (FRDS1), pyruvate carboxylase 1 (PYC1) and pyruvate carboxylase 2 (PYC2) is under the control of a second foreign, constitutively active promotor.

5. An isolated genetically modified yeast, wherein the natural gene malate dehydrogenase 2 (MDH2) is replaced or supplemented by a truncated variant of the gene malate dehydrogenase 2 (MDH2), wherein the truncated variant of the gene malate dehydrogenase 2 (MDH2) codes for a malate dehydrogenase 2 (MDH2) protein that is shortened by the first 12N-terminal amino acids, and wherein the gene fumarase 1 (FUM1) is replaced or supplemented by the gene fumarase 1 (FUM1) from an organism being different from the yeast and wherein the gene soluble fumarase reductase 1 (FRDS1) is overexpressed and wherein one of the genes or both genes pyruvate carboxylase 1 (PYC1) and pyruvate carboxylase 2 (PYC2) are overexpressed.

6. The yeast according to claim 4, wherein the constitutively active promoter of the alcohol dehydrogenase 1 (AHD1) promoter.

* * * * *